(12) United States Patent
Huang (10) Patent No.: US 9,804,098 B2
(45) Date of Patent: Oct. 31, 2017

(54) DEFECT RECOGNITION SYSTEM AND DEFECT RECOGNITION METHOD

(71) Applicant: Taiwan Semiconductor Manufacturing Co., Ltd., Hsinchu (TW)

(72) Inventor: Chun-Jung Huang, Yunlin County (TW)

(73) Assignee: Taiwan Semiconductor Manufacturing Co., Ltd., Hsinchu (TW)

( * ) Notice: Subject to any disclaimer, the term of this patent is extended or adjusted under 35 U.S.C. 154(b) by 139 days.

(21) Appl. No.: 14/887,339

(22) Filed: Oct. 20, 2015

(65) Prior Publication Data

US 2017/0108445 A1 Apr. 20, 2017

(51) Int. Cl.
*G01N 21/88* (2006.01)
*G01N 21/95* (2006.01)

(52) U.S. Cl.
CPC ..... *G01N 21/8851* (2013.01); *G01N 21/9501* (2013.01); *G01N 2021/8864* (2013.01)

(58) Field of Classification Search
CPC ........... G01N 21/8851; G01N 21/9501; G01N 2021/8864
See application file for complete search history.

(56) References Cited

U.S. PATENT DOCUMENTS

| 6,542,830 B1* | 4/2003 | Mizuno | G01R 31/2894 257/E21.525 |
| 2001/0011708 A1* | 8/2001 | Hakamata | A61B 1/00009 250/458.1 |
| 2004/0228515 A1* | 11/2004 | Okabe | G06T 7/0004 382/145 |
| 2010/0085855 A1* | 4/2010 | Yoshida | G11B 20/1883 369/53.41 |
| 2010/0296722 A1* | 11/2010 | Liu | G01N 21/9501 382/149 |
| 2014/0125980 A1* | 5/2014 | Nakao | G01N 21/8806 356/369 |

* cited by examiner

*Primary Examiner* — Sang Nguyen
(74) *Attorney, Agent, or Firm* — JCIPRNET (57) ABSTRACT

A defect recognition system and a defect recognition method are described. The method includes inspecting a wafer to generate a defect map and locating at least one defect on the wafer by using the defect map; measuring at least one light component of light reflected from one of the at least one defect; comparing the at least one light component measured from the light reflected from the defect with a characteristic curve of the corresponding light component of the defect; and estimating an occurrence time of the defect based on the comparison.

18 Claims, 5 Drawing Sheets

DEFECT RECOGNITION SYSTEM AND DEFECT RECOGNITION METHOD

BACKGROUND

In the manufacturing processes of modern semiconductor devices, various materials and machines are manipulated to create a final product. Manufacturers have dedicated to reduce particulate contamination during processing so as to improve product yields. Due to the increasing complexity of semiconductor devices (e.g., many more layers and processes) and the development of larger wafers, the need for defect detection and control is further emphasized.

The inspection on the semi-manufactured product is frequently performed during manufacture by using wafer scanner in order to timely find the defects. The wafer scanner may detect the defects, analyze the defects to identify the types of the defects, and locate the defects on the wafer, so as to assist the operator in evaluating and correcting the manufacturing processes that cause the defects.

However, since there are hundreds of processes in manufacturing the product, the possible factors that cause the defects are considerable and the origin of the defect is hard to derive. As a result, the evaluation of defects highly relies on human knowledge and expertise and costs a large amount of time and efforts, but the result is usually not satisfactory.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

The following disclosure provides many different embodiments, or examples, for implementing different features of the provided subject matter. Specific examples of components and arrangements are described below to simplify the present disclosure.
These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

In manufacturing the semiconductor product, an inspection is performed on a wafer to scan the surface of the wafer by using a light source (e.g., a laser) and measure the light reflected from the surface to detect potential defects. In the present disclosure, the aforesaid reflected light is further directed to a spectrometer analyzer for measuring the light components of reflected light. Since the light components of the reflected light decay along with the time, a characteristic curve of the light component may be derived in advance by collecting measurements of the light component performed at different time periods and used as a reference to compare with a current measurement. Based on the comparison, an approximate time of defect occurrence may be estimated and the manufacturing process that causes the defect may be further determined.

In view of the foregoing, the present disclosure provides a defect recognition system. In some embodiments, the defect recognition system includes a light source, an inspecting component, a light analyzing component and a processing component. The light source is configured to project light on a wafer. The inspecting component is configured to inspect a wafer to generate a defect map and locate at least one defect on the wafer by using the defect map. The light analyzing component is configured to measure at least one light component of the light reflected from one of the at least one defect. The processing component is operatively connected to the inspecting component and the light analyzing component, in which the processing component is programmed to compare the at least one light component measured from the light reflected from the defect with a characteristic curve of the corresponding light component of the defect, and estimate an occurrence time of the defect based on the comparison.

Figure 1:
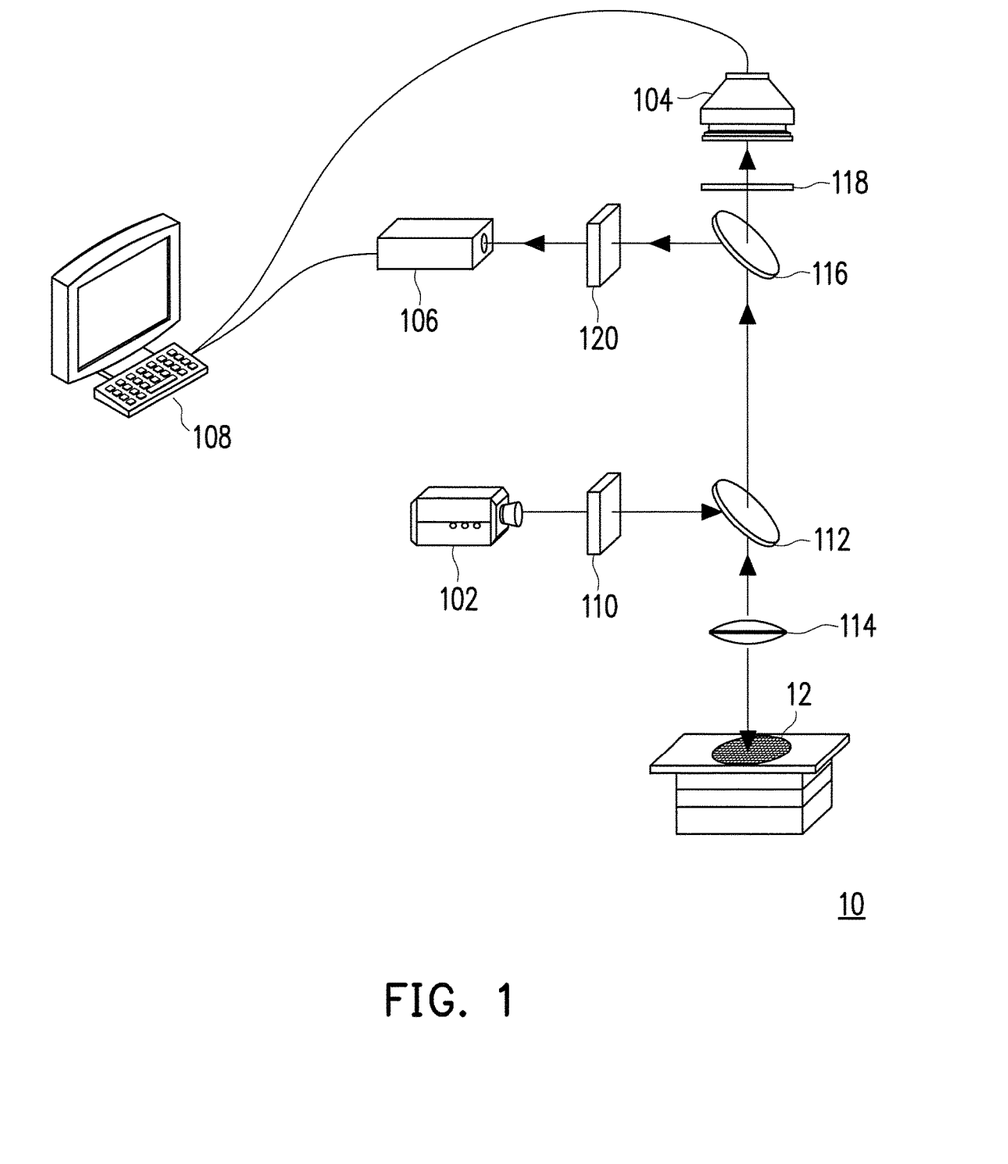
FIG. 1 is a schematic diagram illustrating a defect recognition system in accordance with some embodiments of the present disclosure.

FIG. 1 is a schematic diagram illustrating a defect recognition system in accordance with some embodiments of the present disclosure. In some embodiments, the defect recognition system 10 includes a light source 102, an inspecting component 104, a light analyzing component 106, a processing component 108, and optical components 110, 112, 114, 116, 118 and 120.

In some embodiments, the light source 102 is a laser or other light generators that generate light with various wavelengths. The light source 102 projects light on the wafer 12 such that the light reflected from the wafer 12 can be detected by the inspecting component 104 and the light analyzing component 106 for subsequent inspection and analysis.

In some embodiments, the inspecting component 104 includes a photomultiplier detector or other light sensing elements such as charge-coupled device (CCD), backside illumination (BSI) sensor, or complementary metal-oxidesemiconductor (CMOS) sensor, for detecting the light reflected from the wafer 12 so as to inspect defects on the wafer 12.

In some embodiments, the light analyzing component 106 is a spectrometer analyzer that detects the light reflected from the wafer 12, analyzes a spectrum of the detected light and measures the light components of the reflected light based on the analyzed spectrum. In some embodiments, the light components to be measured include a lightness L*, a color component a*, or a color component b* in a Lab color space, or a combination thereof.

In some embodiments, the processing component 108 is a single-core or a multi-core central processing unit (CPU) or any other programmable general purpose or specific purpose microprocessor, digital signal processor (DSP), programmable controller, application specific integrated circuits (ASIC), programmable logic device (PLD), other similar devices, or a combination of these devices. The processing component 108 is operatively connected to the inspecting component 104 and the light analyzing component 106. In some embodiments, the processing component 108 is configured to access and execute the programs recorded in a computer-readable storage medium, so as to implement a method of defect recognition in accordance with some embodiments of the present disclosure.

As shown in FIG. 1, the light source 102 produces polarized light at discrete wavelengths. The light passes through a filter 110 which isolates the beam of light. The filter 110 may further include optics which expand the beam and then focus the beam on a pinhole aperture. The diameter of the pinhole aperture is selected to allow easy alignment of the beam of light. The light having the selected wavelength (s) passes from the filter 110 to a beam splitter 112 which reflects the light of the proper polarization and directs the light to an objective lens 114. The objective lens 114 demagnifies the light and projects the light on the wafer 12. The light is focused in the focal plane of the objective lens 114.

According to the principles of confocal imaging, the light striking the wafer 12 is scattered and a portion of the light is reflected back to the objective lens 114 and returned through the optical path described above. The returning light passes through the beam splitters 112 and 116 and reaches the filter 118 with a pinhole aperture. The light which passes through the aperture is imaged on the inspecting component 104 which generates a defect map of the wafer 12. The inspecting component 104 further locates the defects on the wafer 12 by using the defect map. On the other hand, as the returning light passes through the beam splitter 116, a portion of light is directed to the filter 120 with a pinhole aperture. The light which passes through the aperture is detected by the light analyzing component 106, which measures the light components of the detected light. The data processed by the inspecting component 104 and the light analyzing component 106 is then transmitted to the processing component 108 for further processing.

Figure 2:
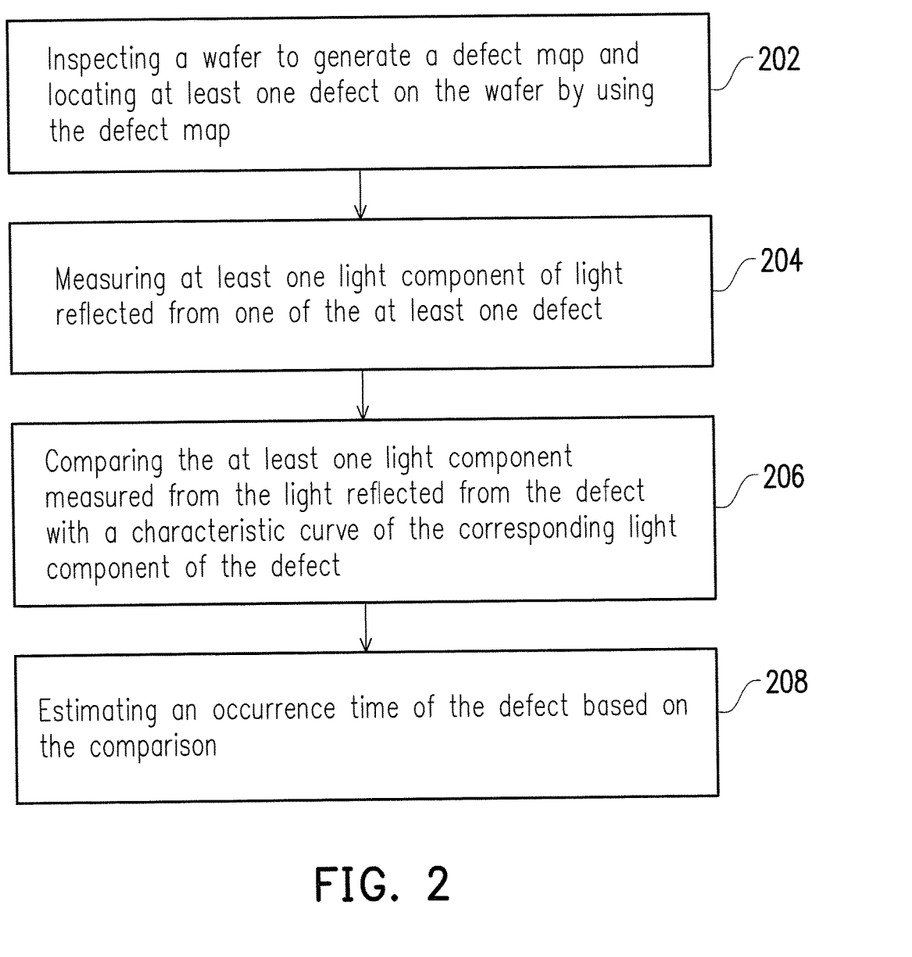
FIG. 2 is a flowchart illustrating a method of defect recognition in accordance with some embodiments of the present disclosure.

In some embodiments, the defect recognition system 10 is adapted for carrying out a method of defect recognition in accordance with some embodiments of the present disclosure. In detail, FIG. 2 is a flowchart illustrating a method of defect recognition in accordance with some embodiments of the present disclosure.

In step 202, the inspecting component 104 inspects the wafer 12 to generate a defect map and locates the defects on the wafer 12 by using the defect map. In some embodiments, the inspecting component 104 scans the wafer 12 by lines to generate data of lines representing light reflected from the lines of the wafer 12, compares a plurality of features of a sample image formed by the data of lines with a corresponding plurality of features of a reference image, and recognizes features in the sample image deviating from corresponding features of the reference image as the defect based on the comparison. In some embodiments, the defect recognition system 10 further includes a computer-readable storage medium (not shown) operably connected to the inspecting component 104 for storing the reference image.

In step 204, the light analyzing component 106 measures at least one light component of light reflected from one of the at least one defect. In some embodiments, the light analyzing component 106 detects the light reflected from the wafer 12, analyzes a spectrum of the detected light so as to measure the light components of the reflected light.

In step 206, the processing component 108 compares the at least one light component measured from the light reflected from one of the at least one defect with a characteristic curve of the corresponding light component of the defect. In step 208, the processing component 108 estimates an occurrence time of the defect based on the comparison in step 206. In detail, in some embodiments, the processing component 108 inquires a characteristic curve of one of the light components and looks up the currently measured light component in the characteristic curve to find a corresponding time period. The characteristic curve records decay of the light component along with time and the time period being found represents how long it takes for the light component to decay from the light component measured when the defect just occurs to the currently measured light component. Therefore, the processing component 108 may obtain the occurrence time of the defect by subtracting the time period from the inspection time of measuring the light component.

In some embodiments, aforesaid characteristic curves of the light components are previously established by the processing component 108 by using historical data of measurements and stored in a computer-readable storage medium (not shown) operably connected to the processing component 108. In detail, taking lightness for example, the processing component 108 collects a plurality of measurements of lightness of the light reflected from the defect measured at different time points and collects the time for performing the measurements. Then, the processing component 108 labels the measurements in a xy-coordinate plane, calculates a trend line of the measurements and uses the trend line as the characteristic curve of lightness. In some embodiments, the values of measurements may be further processed to enhance the variance of the measurements along with time such as calculating contrast values of the measurements or calculating natural log values of the measurements or the contrast values.

In some embodiments, the processing component 108 further inquiries a manufacturing schedule of the wafer 12 with the estimated occurrence time of the defect so as to determine a manufacturing process that causes the defect. In detail, since the manufacturing schedule records the time periods of the manufacturing processes, as the occurrence time (or occurrence date) is estimated, it is easy to find the manufacturing process that causes the defect by simply comparing the estimated occurrence time with the time periods of the manufacturing processes in the manufacturing schedule.

In some embodiments, the processing component 108 estimates the occurrence time of the defect based on the lightness. Accordingly, the processing component 108 inquires a characteristic curve of the lightness, and then looks up the currently measured lightness in the characteristic curve to find a corresponding time period. In some embodiments, the processing component 108 calculates a natural log value of a contrast value of lightness so as compare the natural log value with the characteristic curve of the lightness to find the corresponding time period. Finally, the processing component 108 subtracts the time period from the inspection time of measuring the lightness and obtains the occurrence time of the defect.

Figure 3:
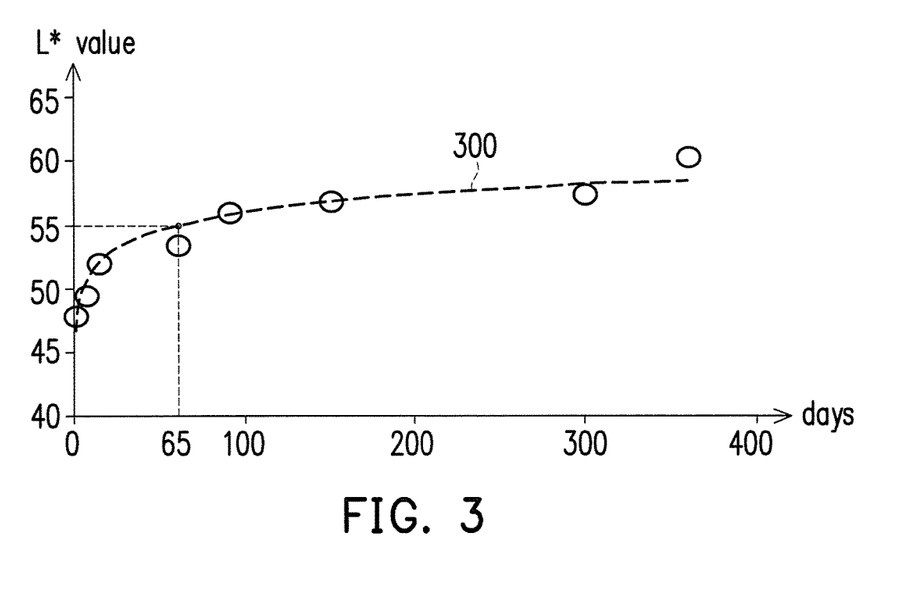
FIG. 3 is a diagram illustrating a characteristic curve of lightness in accordance with some embodiments of the present disclosure.

For example, FIG. 3 is a diagram illustrating a characteristic curve of lightness in accordance with some embodiments of the present disclosure.

In FIG. 3, the horizontal axis represents the time of performing the measurement and the vertical axis represents a contrast value of lightness (i.e., L* value) being measured. The sampling points represent contrast values of the measurements of lightness detected at different time points. The trend line 300 of the sampling points is calculated based on the coordinates of the sampling points by using a regression analysis method. Accordingly, when a current lightness of the light reflected from the defect is measured, the contrast value of the lightness between the lightness with respect to the defect and the lightness with respect to non-defective device in the wafer is calculated and the trend line 300 is looked up by the contrast value so as to find the time period it takes for the lightness to decay. For example, if a contrast value of the currently measured lightness is equal to 55, it is found the corresponding time is about 65 days according to the trend line 300. Therefore, by tracking back 65 days from the day of performing the measurement, the occurrence time of the defect is obtained.

In some embodiments, the processing component 108 estimates the occurrence time of the defect based on the types of the light components. Accordingly, the processing component 108 inquires the characteristic curves of the light components, compares the light components measured from the light reflected from the located defect with the characteristic curves of the corresponding light components of the defect to find corresponding time periods. The processing component 108 respectively subtracts the time periods from the inspection time of measuring the light components to derive the occurrence time of the defect. In some embodiments, the processing component 108 calculates statistics of the occurrence time estimated based on the light components to determine a final result of the occurrence time, in which the statistics is a mean, a median, a standard deviation, a confidence interval (CI), or percentiles.

In some embodiments, the processing component 108 estimates the occurrence time mainly based on measurements of lightness L* and modifies the occurrence time based on measurements of other light components such as color components a* and b*.

Figure 4:
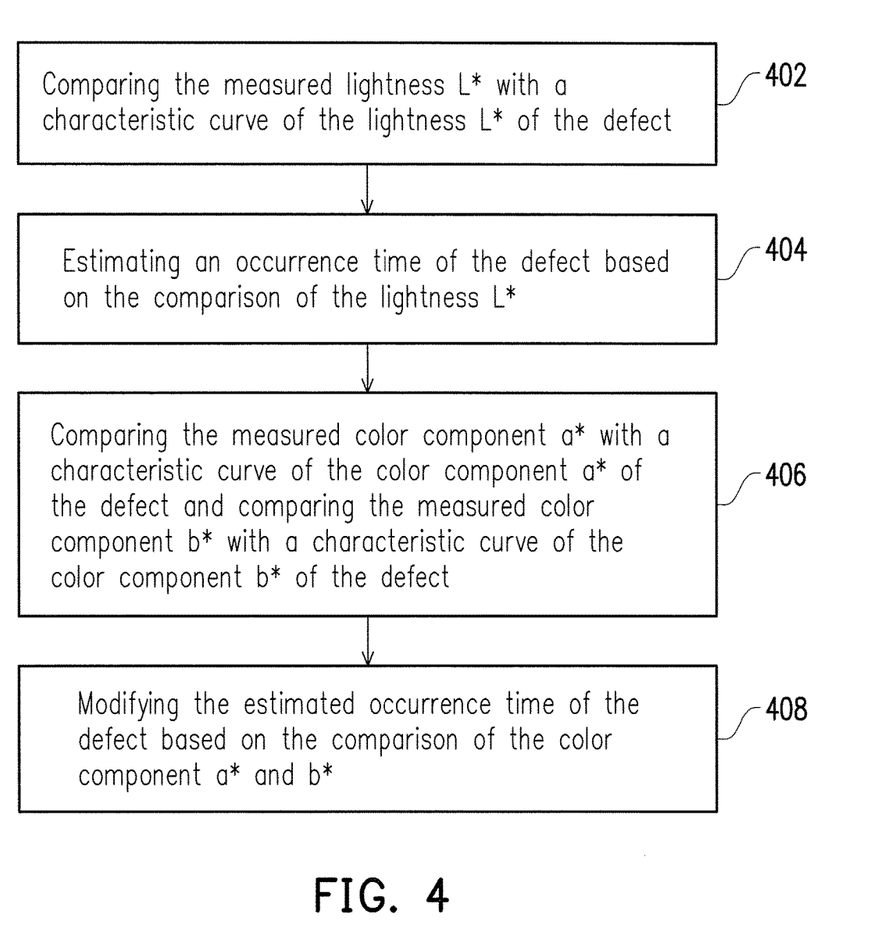
FIG. 4 is a flowchart illustrating a method of defect recognition in accordance with some embodiments of the present disclosure.

For example, FIG. 4 is a flowchart illustrating a method of defect recognition in accordance with some embodiments of the present disclosure.

Referring to FIG. 1 and FIG. 4, in step 402, the processing component 108 compares the measured lightness L* with a characteristic curve of the lightness L* of the defect. In step 404, the processing component 108 estimates the occurrence time based on the comparison of lightness L*. In step 406, the processing component 108 compares the measured color component a* with a characteristic curve of the color component a* of the defect and compares the measured color component b* with a characteristic curve of the color component b* of the defect. In step 408, the processing component 108 modifies the estimated occurrence time based on the comparison of the color components a* and b*.

In some embodiments, the processing component 108 modifies the estimated occurrence time by multiplying the time periods derived based on the lightness and the color components a* and b* with different weights. For example, FIG. 5 is a diagram illustrating a characteristic curve of color component a* in accordance with some embodiments of the present disclosure.

Figure 5:
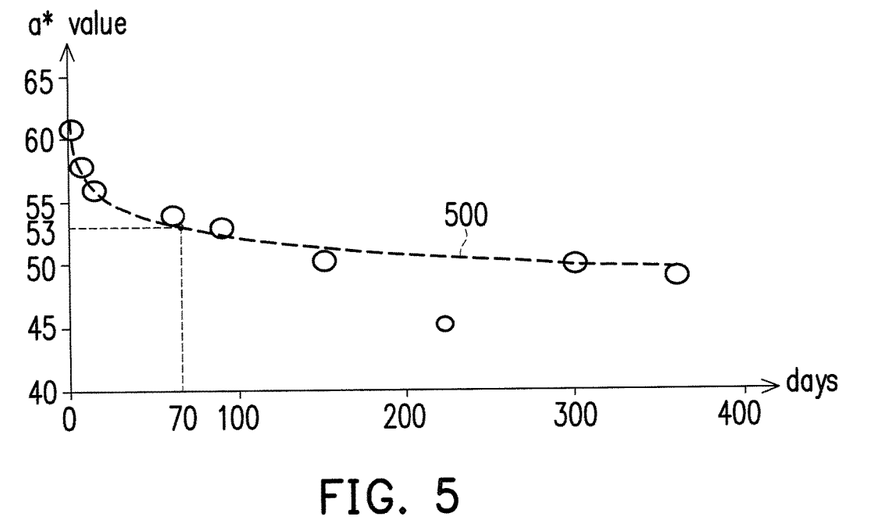
FIG. 5 is a diagram illustrating a characteristic curve of color component a* in accordance with some embodiments of the present disclosure.

In FIG. 5, the horizontal axis represents the time of performing the measurement and the vertical axis represents a natural log value of a contrast value of color component a* (i.e., a* value) in the Lab color space. The sampling points represent the natural log values of contrast values of the measurements of color component a* detected at corresponding time points. The trend line 500 of the sampling points is calculated based on the coordinates of the sampling points by using a regression analysis method. Accordingly, when a current color component a* of the light reflected from the defect is measured, a natural log value of the contrast value of the color component a* between the color component a* with respect to the defect and the color component a* with respect to non-defective device in the wafer is calculated and the trend line 500 is looked up by using the natural log value so as to find the time period it takes for the color component a* to decay. For example, if an a* value of the currently measured color component a* is equal to 53, it is found the corresponding time is about 70 days according to the trend line 500.

In some embodiments, the time period (i.e., 65 days) derived based on the lightness and the time period (i.e., 70 days) derived based on the color component a* are multiplied with weights 80% and 20%, respectively, and a sum of the products (i.e., 65*80%+70*20%=66 days) is calculated and used as a final result of the time period. Finally, the time period is subtracted from the inspection time to obtain the occurrence time of the defect.

In some embodiments, the aforesaid weights of light components are determined based on certain criterions. In some embodiments, a coefficient of determination (i.e., R-squared) indicating how well the data of sampling points fit the calculated trend line is calculated and used as a reference to determine the weights of light components. For example, referring to the embodiments of FIG. 5, a R-squared with respect to color component a* is calculated based on the a* values and the trend line 500 in FIG. 5. If the calculated R-squared is larger than or equal to 0.9, the weight of the color component a* is set as 0.2 while the weight of lightness is set as 0.8. If the calculated R-squared is between 0.7 to 0.9, the weight of the color component a* is set as 0.7 while the weight of lightness is set as 0.3. If the calculated R-squared is less than 0.7, the weight of the color component a* is set as 0, which means the color component a* is not used as a reference to modify the occurrence time estimated based on the comparison of lightness L*.

In some embodiments, the processing component 108 estimates the occurrence time based on multiple defects. In detail, since the defects may appear in group due to same process or same stage, a statistical method is further applied to the occurrence time derived from multiple defects so as to converge the occurrence time of the defects. As a result, a more accurate occurrence time of the defects is obtained.

In some embodiments, the processing component 108 estimates occurrence time of the defects in the defect map by using the method illustrated in the embodiments of FIG. 2. The processing component 108 sorts the estimated occurrence time of the defects in the defect map, and then calculates an interval of a median of the estimated occurrence time with a deviation so as to determine a final result of the occurrence time. In some embodiments, the deviation is equal to a product of a factor and a difference of a 97th percentile and the median of the estimated occurrence time. In some embodiments, the factor is ranging from 1 to k, in which k is an arbitrary number larger than 1 and is determined based on the selection of confidence level. In some embodiments, the factor is equal to 19.6 which is the approximate value of the 97.5 percentile point of the normal distribution and used in the construction of approximate 95% confidence intervals, in which 95% of the area under a normal curve lies within roughly 1.96 standard deviations of the mean. In some embodiments, the factor is equal to a product or a quotient of 1.96 and another experiential or experimental value.

For example, in some embodiments, the processing component 108 calculates an interval T of the occurrence time of defects through following equation:

$$T=P_{50} \pm 1.96 \times (P_{97}-P_{50}) \div 1.88$$

In detail, the interval T is equal to a 50th percentile $P_{50}$ (i.e., a median) of the estimated occurrence time derived based on the defects with a deviation, and the deviation is equal to a product of a factor and a difference between a 97th percentile $P_{97}$ and a 50th percentile $P_{50}$ of the estimated occurrence time derived based on the defects. The factor is equal to a quotient of 1.96 divided by 1.88 which is determined based on experimental results.

In some embodiments, a non-transitory computer-readable medium comprising processor executable instructions that when executed perform a method for recognizing defects on a wafer as illustrated in the embodiments above. In some embodiments, the non-transitory computer-readable medium is a CD-R, a DVD-R, a flash drive, or a platter of a hard disk drive, etc., on which is encoded computer-readable data. The computer-readable data, such as binary data comprising a plurality of zeros and ones, in turn comprises a set of computer instructions configured to operate according to one or more of the principles set forth herein. In some embodiments, the processor-executable computer instructions are configured to perform a method for recognizing defects, such as at least some of the exemplary method illustrated in FIG. 2, for example. Many such computer-readable media are devised by those of ordinary skill in the art that are configured to operate in accordance with the techniques presented herein.

According to some embodiments, a defect recognition system includes a light source configured to project light on a wafer, an inspecting component configured to inspect the wafer to generate a defect map and locate at least one defect on the wafer by using the defect map, a light analyzing component configured to measure at least one light component of light reflected from one of the at least one defect, a processing component operatively connected to the inspecting component and the light analyzing component. The processing component is programmed to compare the at least one light component measured from the light reflected from the defect with a characteristic curve of the corresponding light component of the defect, and estimate an occurrence time of the defect based on the comparison.

According to some embodiments, a defect recognition method includes inspecting a wafer to generate a defect map and locating at least one defect on the wafer by using the defect map, measuring at least one light component of light reflected from one of the at least one defect, comparing the at least one light component measured from the light reflected from the defect with a characteristic curve of the corresponding light component of the defect, and estimating an occurrence time of the defect based on the comparison.

According to some embodiments, a non-transitory computer-readable medium includes processor executable instructions that when executed perform a method for recognizing at least one defect on a wafer. The method includes inspecting the wafer to generate a defect map and locating the at least one defect in the defect map, measuring at least one light component of light reflected from one of the at least one defect, comparing the at least one light component measured from the light reflected from the located defect with a characteristic curve of the corresponding light component of the defect, and estimating an occurrence time of the defect based on the comparison.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A defect recognition system, comprising:
   a light source configured to project light on a wafer;
   an inspecting component configured to inspect the wafer to generate a defect map and locate at least one defect on the wafer by using the defect map;
   a light analyzing component configured to measure at least one light component of light reflected from one of the at least one defect; and
   a processing component operatively connected to the inspecting component and the light analyzing component, wherein the processing component is programmed to:
   compare the at least one light component measured from the light reflected from the defect with a characteristic curve of the corresponding light component of the defect;
   estimate an occurrence time of the defect based on the comparison; and
   subtract a time period corresponding to the measured light component in the characteristic curve from an inspection time of measuring the light component of the defect to obtain the occurrence time of the defect.

2. The defect recognition system of claim 1, wherein the inspecting component scans the wafer by lines to generate data of lines representing light reflected from the lines of the wafer, compares a plurality of features of a sample image formed by the data of lines with a corresponding plurality of features of a reference image, and recognizes features in the sample image deviating from corresponding features of the reference image as the defect based on the comparison.

3. The defect recognition system of claim 2, further comprising a computer-readable storage medium operably connected to the inspecting component, wherein the storage medium stores the reference image.

4. The defect recognition system of claim 1, wherein the processing component is configured to inquire a manufacturing schedule with the occurrence time of the defect to determine a manufacturing process that causes the defect.

5. The defect recognition system of claim 1, wherein the at least one light component comprises a lightness L*, a color component a*, or a color component b* in a Lab color space, or a combination thereof.

6. The defect recognition system of claim 5, wherein the processing component is configured to compare the measured lightness L* with a characteristic curve of the lightness L* of the defect to estimate the occurrence time, and compare the measured color component a* with a characteristic curve of the color component a* of the defect and comparing the measured color component b* with a characteristic curve of the color component b* of the defect to modify the estimated occurrence time.

7. The defect recognition system of claim 6, further comprising a computer-readable storage medium operably connected to the processing component, wherein the storage medium stores the characteristic curve of the light component of the at least one defect.

8. The defect recognition system of claim 1, the processing component is configured to calculate a natural log value of a contrast value of the at least one light component so as compare the natural log value with the characteristic curve of the corresponding light component.

9. The defect recognition system of claim 1, the processing component is configured to sort the estimated occurrence time of the at least one defect in the defect map and calculate an interval of a median of the estimated occurrence time with a deviation so as to determine a final result of the occurrence time.

10. A defect recognition method, comprising:
inspecting, by an inspecting component, a wafer to generate a defect map and locating at least one defect on the wafer by using the defect map;
measuring, by a light analyzing component, at least one light component of light reflected from one of the at least one defect;
comparing, by a processing component, the at least one light component measured from the light reflected from the defect with a characteristic curve of the corresponding light component of the defect;
estimating, by the processing component, an occurrence time of the defect based on the comparison; and
subtracting, by the processing component, a time period corresponding to the measured light component in the characteristic curve from an inspection time of measuring the light component of the defect to obtain the occurrence time of the defect.

11. The method of claim 10, wherein the step of inspecting, by the inspecting component, the wafer to generate the defect map and locating the at least one defect in the defect map comprises:
scanning the wafer by lines to generate data of lines representing light reflected from the lines of the wafer;
comparing a plurality of features of a sample image fonned by the data of lines with a corresponding plurality of features of a reference image; and
recognizing features in the sample image deviating from corresponding features of the reference image as the defect based on the comparison.

12. The method of claim 10, further comprising:
inquiring a manufacturing schedule with the occurrence time of the defect to determine a manufacturing process that causes the defect.

13. The method of claim 10, wherein the at least one light component comprises a lightness L*, a color component a*, or a color component b* in a Lab color space, or a combination thereof.

14. The method of claim 13, wherein the steps of comparing, by the processing component, the at least one light component measured from the light reflected from the defect with a characteristic curve of the corresponding light component of the defect, and estimating an occurrence time of the defect based on the comparison comprise:
comparing the measured lightness L* with a characteristic curve of the lightness L* of the defect to estimate the occurrence time; and
comparing the measured color component a* with a characteristic curve of the color component a* of the defect and comparing the measured color component b* with a characteristic curve of the color component b* of the defect to modify the estimated occurrence time.

15. The method of claim 14, wherein before the step of comparing, by the processing component, the at least one light component measured from the light reflected from the located defect with the characteristic curve of the corresponding light component of the defect, the method further comprises:
collecting a plurality of measurements of one of the at least one light component of the light reflected from the defect and time for performing the measurements; and
calculating a trend line of the measurements of the light component and time for performing the measurements as the characteristic curve of the light component.

16. The method of claim 10, wherein the step of comparing, by the processing component, the at least one light component measured from the light reflected from the defect with the characteristic curve of the corresponding light component of the defect comprises:
calculating a natural log value of a contrast value of the at least one light component and comparing the natural log value with the characteristic curve of the corresponding light component.

17. The method of claim 16, wherein after the step of estimating, by the processing component, the occurrence time of the defect based on the comparison, the method further comprises:
sorting the estimated occurrence time of the at least one defect in the defect map; and
calculating an interval of a median of the estimated occurrence time with a deviation to determine a final result of the occurrence time.

18. A non-transitory computer-readable medium comprising processor executable instructions that when executed perform a method for recognizing at least one defect on a wafer, the method comprising:
inspecting, by an inspecting component, the wafer to generate a defect map and locating the at least one defect in the defect map;
measuring, by a light analyzing component, at least one light component of light reflected from one of the at least one defect;
comparing, by a processing component, the at least one light component measured from the light reflected from the defect with a characteristic curve of the corresponding light component of the defect;
estimating, by the processing component, an occurrence time of the defect based on the comparison; and
subtracting, by the processing component, a time period corresponding to the measured light component in the characteristic curve from an inspection time of measuring the light component of the defect to obtain the occurrence time of the defect.

* * * * *